(12) United States Patent
Hakamata et al.

(10) Patent No.: US 7,750,307 B2
(45) Date of Patent: Jul. 6, 2010

(54) RADIATION IMAGE CAPTURING APPARATUS

(75) Inventors: Kazuo Hakamata, Odawara (JP);
Hajime Nakata, Minami-ashigara (JP);
Kuniaki Miyako, Minami-ashigara (JP);
Yasunori Ohta, Yokohama (JP); Yuto Tanaka, Kawasaki (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/238,748

(22) Filed: Sep. 26, 2008

(65) Prior Publication Data
US 2009/0086890 A1     Apr. 2, 2009

(30) Foreign Application Priority Data
Sep. 28, 2007   (JP)   ............................. 2007-252837

(51) Int. Cl.
*G01T 1/24*   (2006.01)
(52) U.S. Cl. ................................. 250/370.09
(58) Field of Classification Search ............. 250/370.09
See application file for complete search history.

(56) References Cited

U.S. PATENT DOCUMENTS

| 6,195,267 B1 * | 2/2001 | MacDonald et al. ........ 361/800 |
| 6,881,961 B2 | 4/2005 | Watanabe |
| 2005/0212935 A1 | 9/2005 | Watanabe et al. |

FOREIGN PATENT DOCUMENTS

| JP | 2003-014860 A | 1/2003 |
| JP | 2005-283262 A | 10/2005 |

* cited by examiner

*Primary Examiner*—Constantine Hannaher
(74) *Attorney, Agent, or Firm*—Sughrue Mion, PLLC (57) ABSTRACT

A radiation image capturing apparatus includes a conductive gel member disposed between a radiation detector and an integrated circuit provided in vicinity of the radiation detector and electrically connected thereto. The conductive gel member blocks the electromagnetic noise generated by the integrated circuit and thereby prevents the electromagnetic noise from propagating to the radiation detector. As a result, the electrical signals generated by the radiation detector are prevented from being affected by the electromagnetic noise and high-quality radiation images can be acquired.

3 Claims, 9 Drawing Sheets

RADIATION IMAGE CAPTURING APPARATUS

BACKGROUND OF THE INVENTION

1. Field of the Invention

The present invention relates to a radiation image capturing apparatus including a radiation detector for detecting a radiation image of a subject as electrical charge information and generating an electrical signal representing the electrical charge information. More particularly, the present invention relates to a radiation image capturing apparatus capable of protecting the radiation detector from electromagnetic noise.

2. Description of the Related Art

In the medical field, radiation image capturing apparatus is extensively used, which exposes a subject (patient) to radiation and receives the radiation that has passed through the subject with a radiation detector to capture a radiation image. Examples of known radiation detectors that can be utilized in the radiation image capturing apparatuses include conventional radiation films that are exposed to record radiation images, and stimulable phosphor panels that store a radiation image into a phosphor in the form of radiation energy and allow the radiation image to be retrieved as stimulated light when exposed to stimulating light. In order to provide a visible radiation image, in the former case, the radiation film, on which radiation images are recorded, is developed using a development device. In the latter case, the stimulable phosphor panel is supplied to a reading apparatus to allow readout of the radiation image.

In environments such as operating rooms, however, rapid readout and display of the radiation image from the radiation detector after acquisition of the image are required to enable prompt and suitable treatment. To meet such requirements, radiation detectors employing solid-state elements have been developed. Such detectors convert radiation either directly into electrical signals or first into visible light with a scintillator and then into electrical signals.

Whichever of above-mentioned radiation detector types is used, only a small analog signal is generated. The small analog signal is generally amplified by an amplifier disposed in the vicinity of the radiation detector. If the analog signal includes noise, however, this noise is also amplified, and the S/N ratio of the signal drops. To address this problem, Japanese Laid-Open Patent Publication No. 2005-283262, for example, has proposed a measure to counter noise on the analog signal generated by the radiation detector.

The Japanese Laid-Open Patent Publication No. 2005-283262 discloses, as shown in FIG. 1 thereof, an image detector in which an amplifier circuit 8 is held between cushioning materials 16 and 17. The cushioning material 16 prevents propagation of mechanical vibration from a cooling system 15 to the amplifier circuit 8, while the cushioning material 17 prevents propagation of mechanical vibration from a substrate holder 4 to the amplifier circuit 8 (see paragraph 0032 and the like of the Japanese Laid-Open Patent Publication No. 2005-283262).

In addition to preventing the effect of mechanical noise such as mechanical vibration, it is also necessary to prevent electromagnetic noise from affecting the radiation detector. In Japanese Laid-Open Patent Publication No. 2005-283262, however, silicone thermal-conductive gel is used for the cushioning material 16, and silicone heat insulating material for the cushioning material 17 (see paragraph 0030 of the Japanese Laid-Open Patent Publication No. 2005-283262), and thus no consideration is given to electromagnetic noise. However, the presence of electromagnetic noise on the analog signal from the radiation detector causes degradation in the quality of the generated radiation image.

SUMMARY OF THE INVENTION

It is an object of the invention to provide a radiation image capturing apparatus capable of preventing electromagnetic noise from affecting electrical signals generated by a radiation detector to allow acquisition of high-quality radiation images.

A radiation image capturing apparatus according to the invention includes a radiation detector for detecting a radiation image of a subject as charge information and generating an electrical signal representing the charge information, an integrated circuit disposed in the vicinity of the radiation detector and electrically connected thereto, and a conductive gel member disposed between the radiation detector and the integrated circuit.

According to the invention, the conductive gel member disposed between the radiation detector and the integrated circuit blocks the electromagnetic noise generated by the integrated circuit and thereby prevents the electromagnetic noise from propagating to the radiation detector. As a result, the electrical signals generated by the radiation detector are prevented from being affected by the electromagnetic noise and high-quality radiation images can be acquired.

Preferably, the conductive gel member surrounds the integrated circuit. Since the conductive gel member is deformable, it can surround the integrated circuit easily and reliably, allowing suitable shielding of the detector from the electromagnetic noise with a simple structure.

The conductive gel member may contain at least one of carbon and silver, so that high conductivity can be realized.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Figure 1:
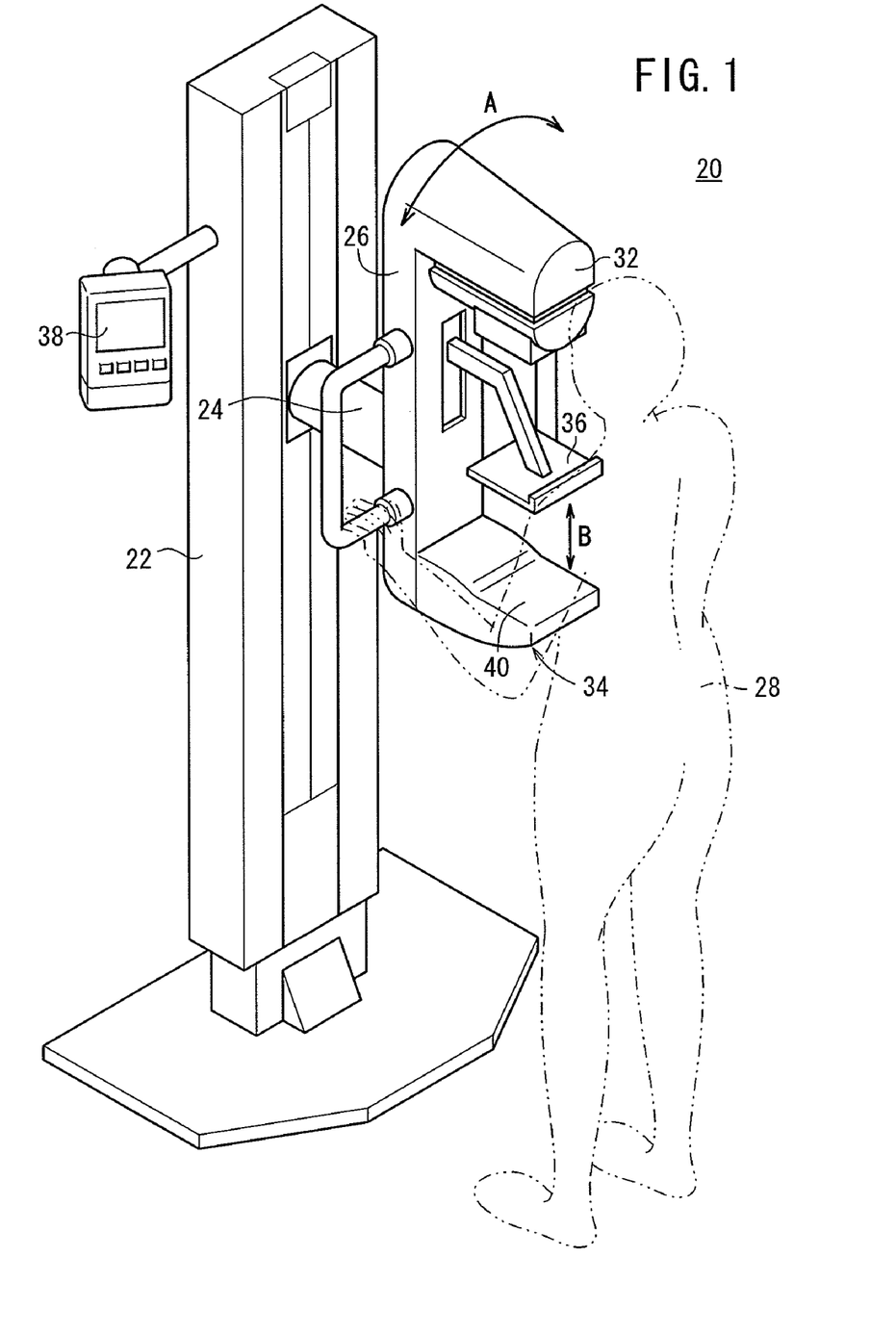
FIG. 1 is a perspective view of a mammography apparatus forming a radiation image capturing apparatus according to an embodiment of the present invention.

FIG. 1 is a perspective view of a radiation image capturing apparatus according to an embodiment of the present invention, which is a mammography apparatus 20 for breast cancer screening or the like.

The mammography apparatus 20 includes an upstanding base 22, an arm 26 fixed to a pivot shaft 24 that is connected substantially centrally to the base 22, a radiation source housing unit 32 fixed to one end of the arm 26 and housing a radiation source (not shown) for applying radiation X to a breast 30 (see FIG. 2) which is the image capturing site of a subject 28, an image capturing base 34 fixed to the other end of the arm 26 so as to oppose to the radiation source housing unit 32, and a compression plate 36 for holding the breast 30 by compressing it against the image capturing base 34.

The arm 26 holding the radiation source housing unit 32 and the image capturing base 34 can be rotated about the pivot shaft 24 in the directions indicated by double-headed arrow A to adjust the image capturing direction of the breast 30 of the subject 28. The compression plate 36 is connected to the arm 26 between the radiation source housing unit 32 and the image capturing base 34 so as to be movable in the directions shown by double-headed arrow B.

The base 22 is also provided with a display control panel 38 for displaying image capturing information obtained by the mammography apparatus 20 and the identification (ID) information or the like of the subject 28. The image capturing information includes the image capturing site, image capturing direction, or the like of the subject 28. The display control panel 38 also allows settings of the above-mentioned information, if desired.

Figure 2:
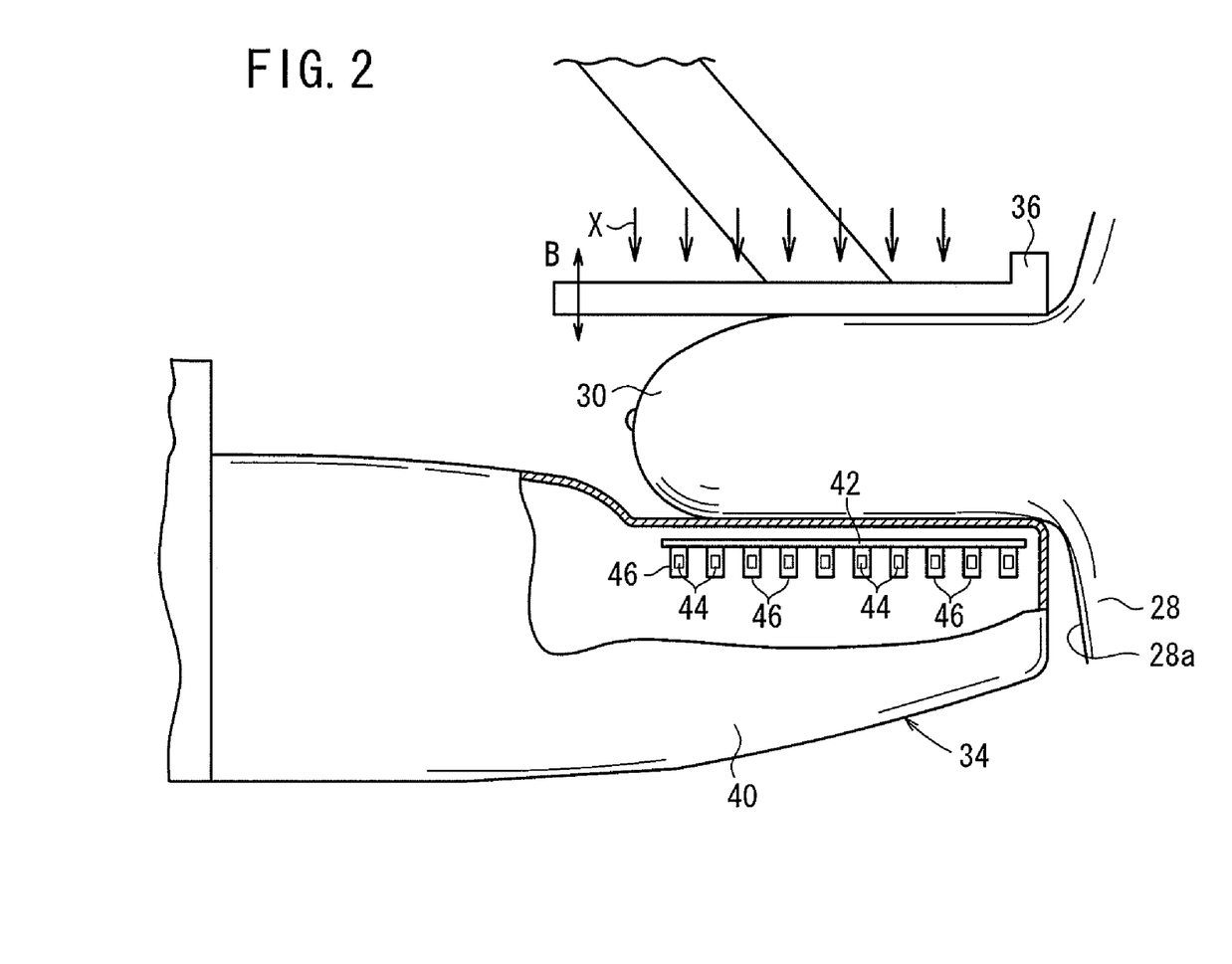
FIG. 2 is a partially cross-sectional side view of main part of the mammography apparatus of FIG. 1, showing an internal structure of an image capturing base.
Figure 3:
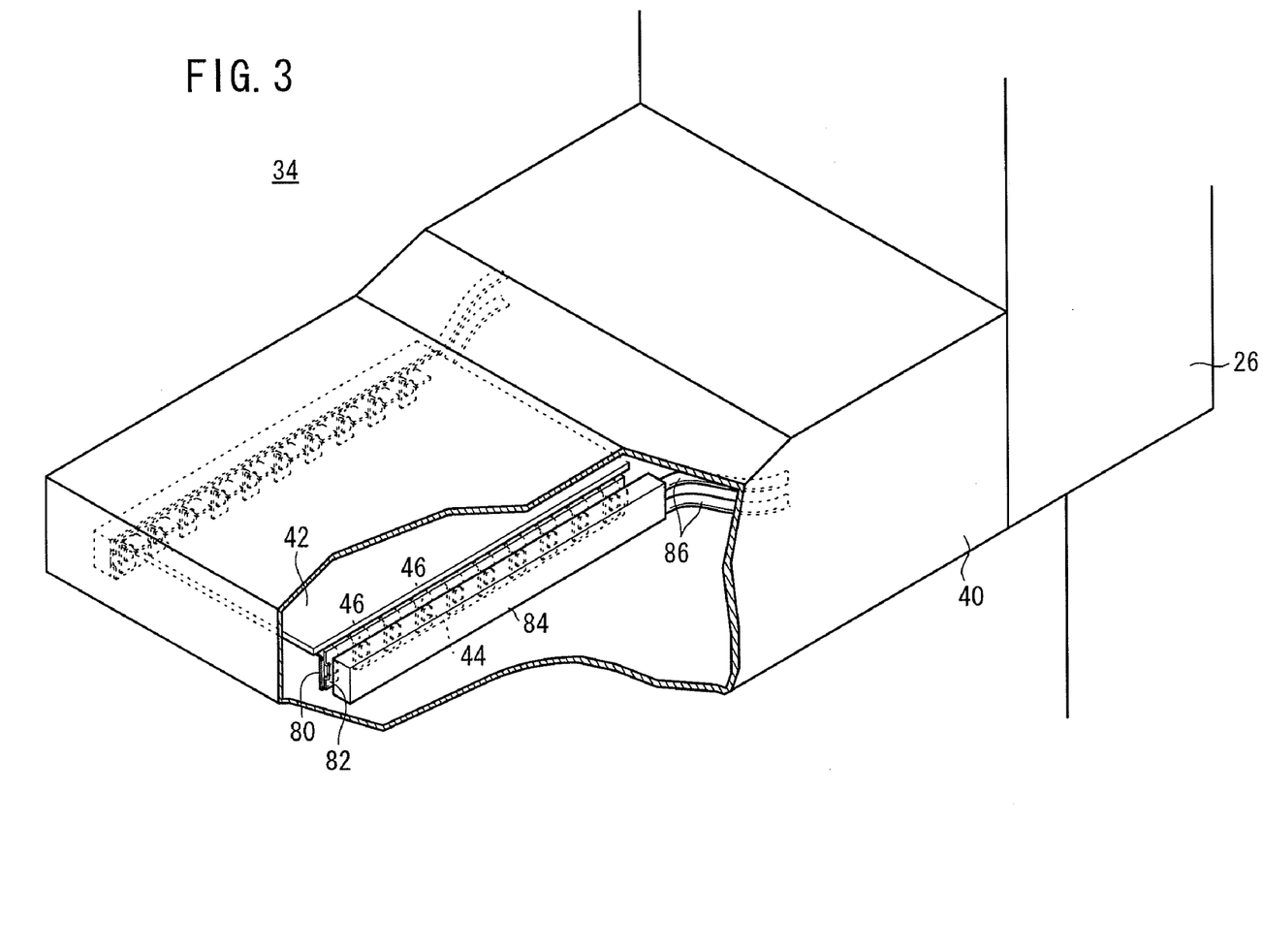
FIG. 3 is a partially cut-away perspective view of the image capturing base, showing the internal structure thereof.

FIG. 2 is a partially cross-sectional side view of main part of the mammography apparatus 20, showing the internal structure of the image capturing base 34. FIG. 2 shows the image capturing site of the subject 28, i.e. the breast 30, placed between the image capturing base 34 and the compression plate 36. FIG. 3 is a partially cut-away perspective view of the image capturing base 34 of FIG. 2, showing the internal structure thereof.

As shown in FIGS. 2 and 3, a housing 40 of the image capturing base 34 contains a planar radiation detector 42. The radiation detector 42 generates electrical signals associated with radiation image information obtained based on the radiation X emitted from the radiation source in the radiation source housing unit 32. Also contained within the housing 40 are a plurality of ASICs (Application Specific Integrated Circuits) 44 for controlling the radiation detector 42, and a plurality of flexible substrates 46 for connecting the ASICs 44 to the radiation detector 42.

Figure 4:
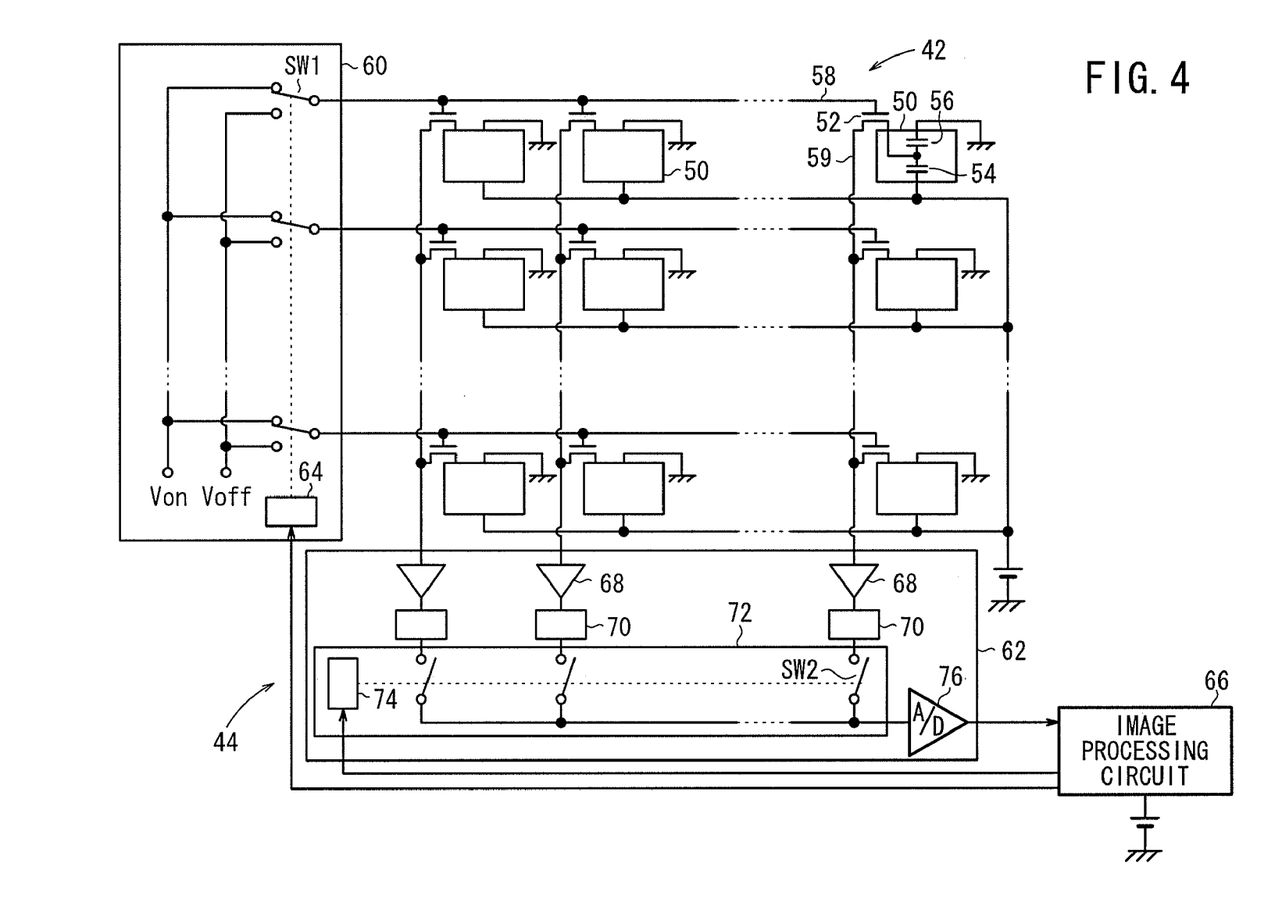
FIG. 4 is a block diagram illustrating a circuit configuration of a radiation detector and components therearound.

FIG. 4 is a block diagram illustrating a circuit configuration of the radiation detector 42 and the ASICs 44. The radiation detector 42 includes a two-dimensional array of pixels 50. Each pixel 50 is provided with a thin film transistor (TFT) 52. Alternatively, the radiation detector 42 may include another device such as a charge coupled device (CCD) or a complementary metal oxide semiconductor (CMOS) sensor. Each ASIC 44 includes a driving circuit 60 for selecting the pixel 50 to be read out, and a reading circuit 62 for reading out charge information from the selected pixel 50. Note that the charge information corresponds to the amount of radiation X detected by each pixel 50.

Each pixel 50 includes a photoelectric conversion layer 54 placed over the array of TFTs 52. The photoelectric conversion layer 54 is made of a material such as amorphous selenium (a-Se), which generates electrical charge upon sensing radiation X. The generated charge is stored into a storage capacitor 56. Then, the TFTs 52 in each row of the two-dimensional array are sequentially switched on to allow the charges in the storage capacitors 56 to be output as image signals. FIG. 4 only illustrates the connection between one TFT 52 and one pixel 50 which is made up of one storage capacitor 56 and the photoelectric conversion layer 54. The details of other pixels 50 are omitted for clarity. Note that the amorphous selenium shows performance degradation at high temperatures because of an inherent structural change and the amorphous selenium must therefore be used within a predetermined temperature range. Hence, a means for cooling the radiation detector 42 is preferably provided within the housing 40 of the image capturing base 34.

The TFT 52 of each pixel 50 is connected to a gate line 58 and a signal line 59 that extend, respectively, in the row direction and in the column direction of the TFT array. Each gate line 58 is connected to the driving circuit 60, and each signal line 59 is connected to the reading circuit 62.

The driving circuit 60 supplies to the gate lines 58 control signals Von and Voff for switching on and off the TFTs 52 arranged in the row direction. The driving circuit 60 includes a plurality of switches SW1 for switching the gate lines 58, and an address decoder 64 for generating a selection signal for selecting one of the switches SW1. The address decoder 64 is provided with an address signal from an image processing circuit 66 disposed in the housing 40.

The signal line 59 receives the charge stored in the storage capacitor 56 of each pixel 50 through the TFTs 52 arranged in the column direction. The charge flows through the signal line 59 and is amplified by an amplifier 68 in the reading circuit 62. The amplifier 68 is connected via a sample-and-hold circuit 70 to a multiplexer 72 of the reading circuit 62. The multiplexer 72 includes a plurality of switches SW2 for switching the signal lines 59, and an address decoder 74 that generates a selection signal for selecting one of the switches SW2. The address decoder 74 is provided with an address signal from the image processing circuit 66. The multiplexer 72 is connected to an analog/digital (A/D) converter 76 that converts the radiation image data into digital signals, which are provided to the image processing circuit 66.

Figure 5:
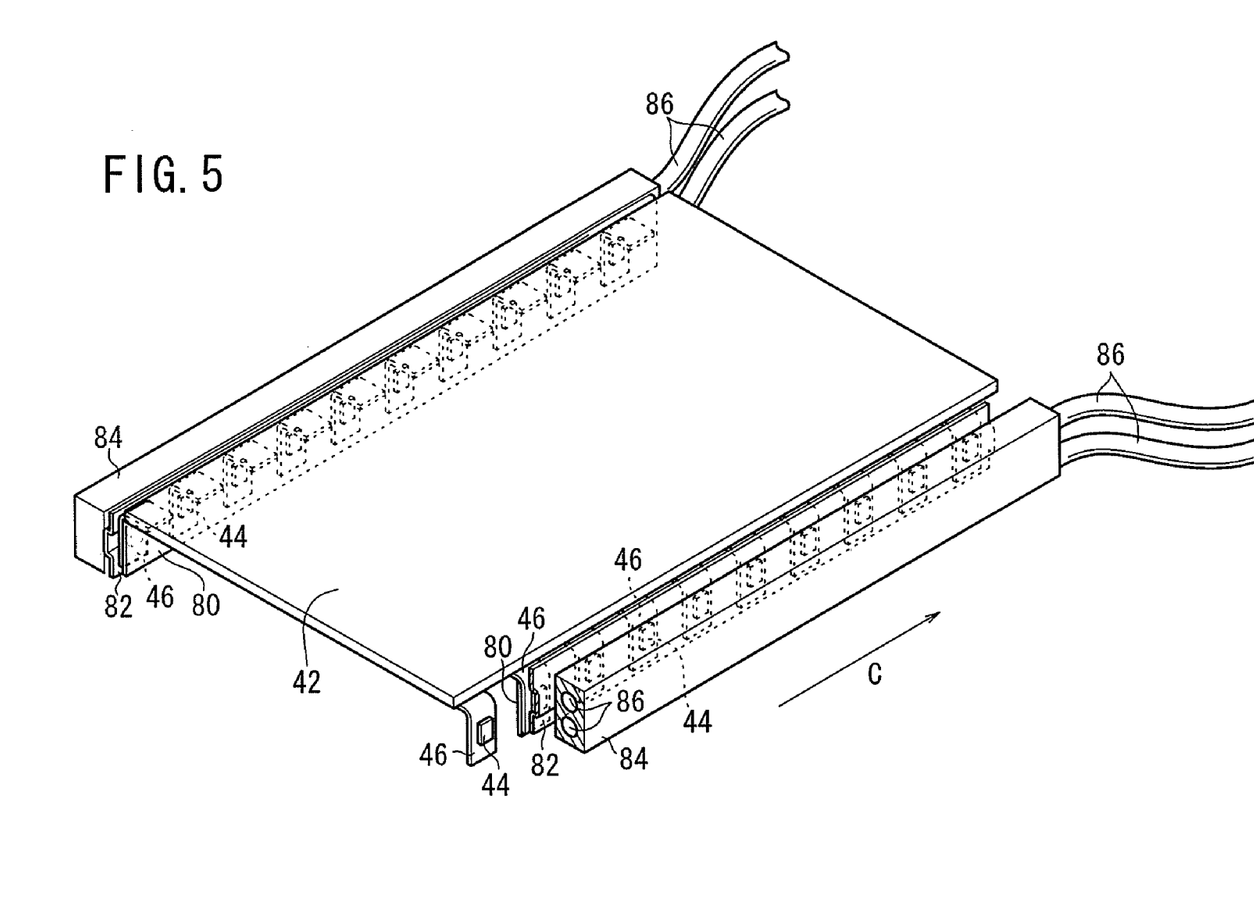
FIG. 5 is a partially cut-away perspective view of the radiation detector and the components therearound.
Figure 6:
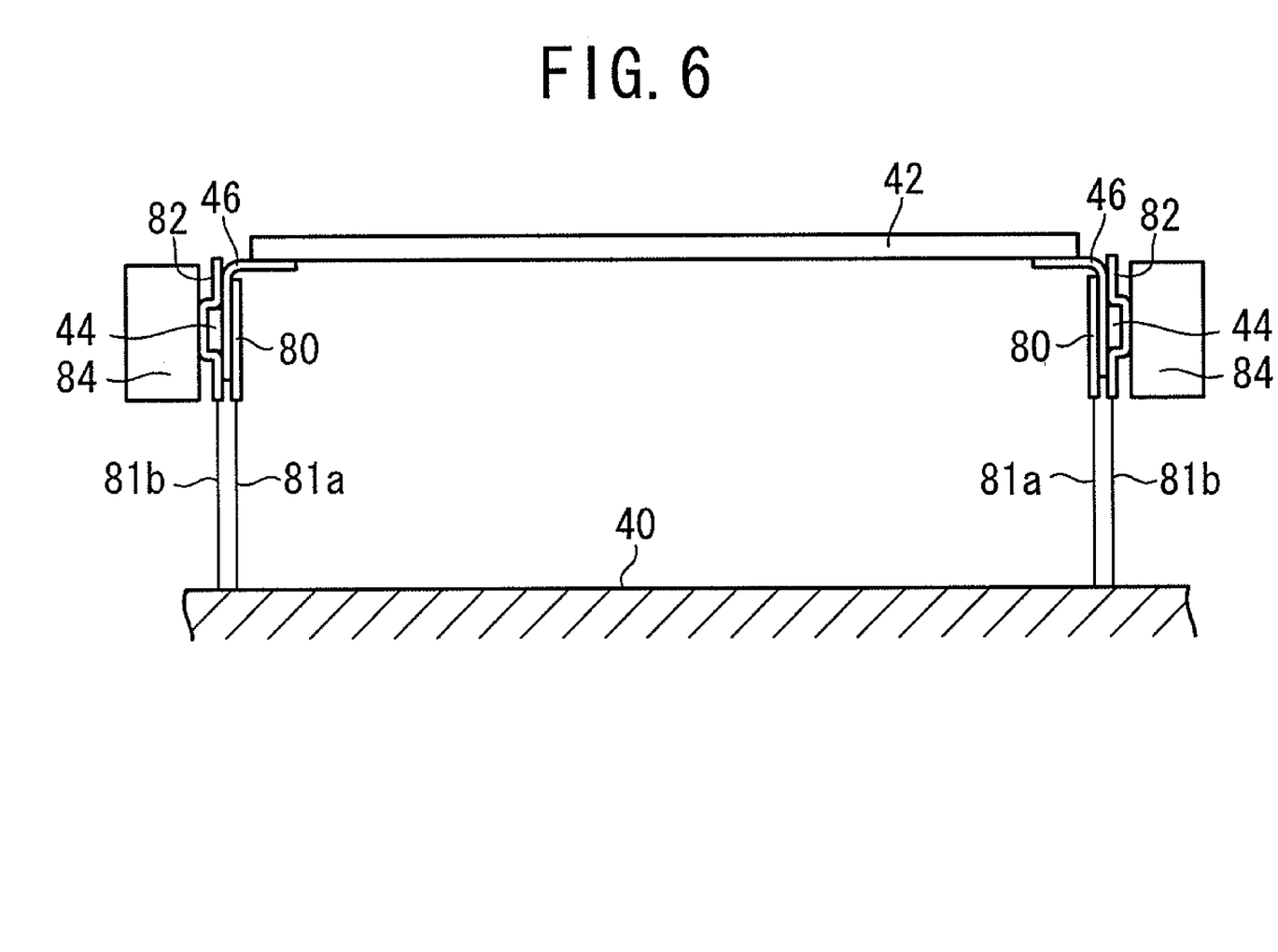
FIG. 6 is a schematic view of the radiation detector and the components therearound looking from a subject's chest wall side toward a pivot shaft side.

FIG. 5 is a partially cut-away perspective view illustrating the radiation detector 42 and the components therearound. FIG. 6 is a schematic view of the radiation detector 42 and the components therearound looking from a chest wall 28a of the subject 28 (see FIG. 2) toward the pivot shaft 24 (in the direction of arrow C in FIG. 5).

As can be seen in FIGS. 5 and 6, each side of the radiation detector 42 is connected to the ASICs 44 via the flexible substrates 46. Each side of the radiation detector 42 has a first conductive gel member 80 of a sheet-like shape disposed between the radiation detector 42 and the ASICs 44. In the present embodiment, the first conductive gel members 80 contain carbon and/or silver, and have thermal-insulating properties. The first conductive gel members 80 are electrically connected, via cables 81a, to the housing 40 that is at a constant potential (ground in the present embodiment). With this arrangement, the first conductive gel members 80 serve as a shield against the electromagnetic noise generated by the ASIC 44. Note that the first conductive gel members 80 may be connected directly to the housing 40.

In addition to the above, the ASICs 44 are also provided on external sides thereof with a second conductive gel member 82 having a sheet-like shape. The second conductive gel members 82 contain carbon and/or silver, and have thermal conductivity. The exposed region of each ASIC 44 (the region that is not in contact with the flexible substrate 46) is surrounded by the second conductive gel member 82. As with the first conductive gel members 80, the second conductive gel members 82 are electrically connected, via cables 81b, to the housing 40 that is at a constant potential. Thus, the second conductive gel members 82 serve as a shield against the electromagnetic noise generated by the ASICs 44, and each ASIC 44 is completely surrounded by the first and second conductive gel members 80 and 82.

As shown in FIGS. 5 and 6, a cooling jacket 84 is attached to the external side of the second conductive gel member 82. The cooling jacket 84 is supplied with coolant from a coolant supply unit (not shown) through a circulating pipe 86 so that the ASICs 44 can be cooled. The coolant supplied to the cooling jacket 84 flows back to the coolant supply unit through the circulating pipe 86. The coolant is cooled in the coolant supply unit and provided again to the cooling jacket 84.

The operation of the mammography apparatus 20 according to the present embodiment, which is basically configured as described above, will now be described.

First, ID information about the subject 28, image capturing conditions, and the like are provided to the mammography apparatus 20 through a console (not shown), an ID card, or the like. The ID information may include the name, age, gender, etc. of the subject 28 and can be acquired from an ID card of the subject 28. If the mammography apparatus 20 is connected to a network, the ID information may also be acquired from other apparatuses on the network. The image capturing conditions may include an image capturing site, an image capturing direction and the like specified by the physician. These items of information may be acquired from a higher-level apparatus on the network or entered through the console by a radiologist. The ID information, image capturing conditions, and the like may be displayed on the display control panel 38 of the mammography apparatus 20 for verification.

The radiologist then sets the mammography apparatus 20 in accordance with specified image capturing conditions. The image capturing directions of the breast 30 may include, for example, a craniocaudal view (CC), a mediolateral view (ML), and a mediolateral oblique view (MLO), in which image is captured by exposing the breast 30 to the X-ray from the top, the side, and an oblique angle respectively. The arm 26 is rotated about the pivot shaft 24 in accordance with the specified image capturing direction.

Next, the breast 30 of the subject 28 is positioned with respect to the mammography apparatus 20. That is, the breast 30 is placed on the image capturing base 34 and the compression plate 36 is moved down to hold the breast 30 between the image capturing base 34 and the compression plate 36 (see FIG. 2).

After the above preparatory operations have been completed, the radiation source (not shown) in the radiation source housing unit 32 is activated to expose the breast 30 to radiation X in accordance with the set image capturing conditions. The radiation X that has passed through the breast 30 charges the radiation detector 42 to form a latent image thereon. The charge is read out by means of the driving circuit 60 and reading circuit 62 of the ASIC 44.

During the operation of the driving circuit 60 and reading circuit 62 of the ASIC 44, electromagnetic noise may be generated. This electromagnetic noise may decrease the signal-to-noise (S/N) ratio of the analog signal generated by the radiation detector 42, and hence degrade the quality of the radiation image.

In the present embodiment, the electromagnetic noise from the ASICs 44 is prevented from affecting the radiation detector 42 by means of the first and second conductive gel members 80 and 82. That is, the first and second conductive gel members 80 and 82 will serve as shields against any electromagnetic noise even if it may be generated.

As explained above, in the present embodiment, the first conductive gel member 80 is placed between the radiation detector 42 and the ASIC 44. The first conductive gel member 80 serves as a shield against the electromagnetic noise from the ASIC 44 and prevents the electromagnetic noise from propagating to the radiation detector 42. Therefore, the analog signal output from the radiation detector 42 is not affected by the electromagnetic noise, and the mammography apparatus 20 can produce high-quality radiation images.

According to the above-described embodiment of the invention, the ASIC 44 is surrounded by the first conductive gel member 80 and the second conductive gel member 82. The first and second conductive gel members 80 and 82 are deformable and can surround the ASIC 44 easily and reliably. Thus, with a simple structure, an enhanced shield against electromagnetic noise can be provided.

The present invention is not limited to the embodiment described above. Various modifications and variations may be made based on the description herein. For example, the invention can be applied to any of the following forms.

The radiation image capturing apparatus to which the above-described embodiment can be applied is not limited to the mammography apparatus 20, but may also be other types of radiation image capturing apparatus such as those that utilize electronic cassettes.

Instead of the radiation detector 42 including a photoelectric conversion layer that converts radiation X directly into an electrical signal corresponding to the amount of the radiation X applied thereto, the embodiment of the invention may be applied to employ a radiation detector that includes a scintillator for converting radiation X into visible light, and a photoconductive recording layer for generating electrical charge pairs when exposed to the visible light.

In the above-mentioned embodiment, the ASIC 44 includes both of the driving circuit 60 and the reading circuit 62. The driving circuit 60 and the reading circuit 62, however, may be provided in separate ASICs 44. Further, the location of the ASICs 44 may be varied, if desired.

Figure 7:
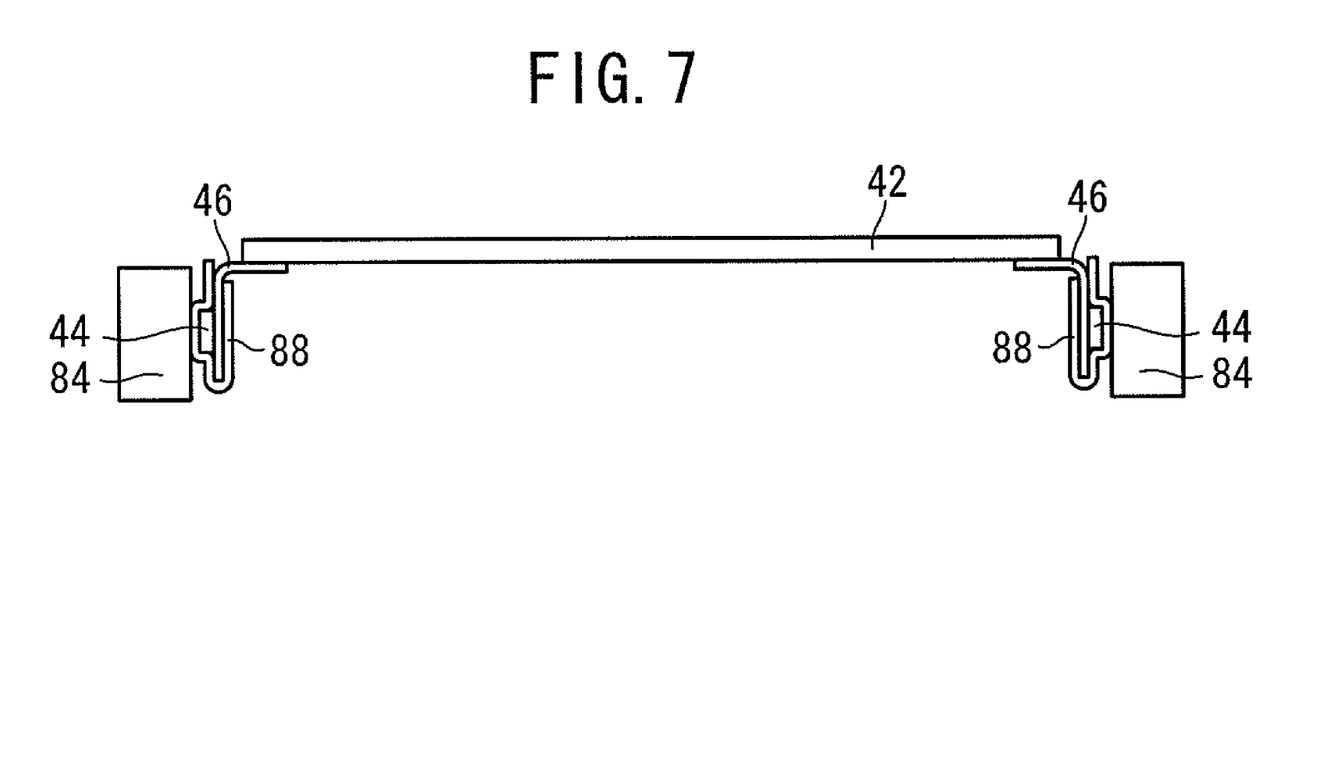
FIG. 7 is a schematic view of the radiation detector and the components therearound according to a first modification of the radiation image capturing apparatus of the invention.

The conductive gel member disposed between the radiation detector 42 and the ASIC 44, i.e. the first conductive gel member 80, may have thermal conductivity instead of thermal insulating properties. As shown in FIG. 7, for example, the ASIC 44 may be substantially completely surrounded by a single sheet conductive gel member 88 having thermal conductivity, and the conductive gel member 88 may be brought in contact with the cooling jacket 84. In this arrangement, heat is transmitted to and absorbed by the cooling jacket 84 not only from the portion of the conductive gel member 88 held between the ASIC 44 and the cooling jacket 84 (i.e., the portion corresponding to the second conductive gel member 82 in FIG. 6), but also from the portion located between the radiation detector 42 and the ASIC 44 (i.e., the portion corresponding to the first conductive gel member 80 in FIG. 6). Therefore, efficient cooling of the portion of the conductive gel member 88 between the radiation detector 42 and the ASIC 44 can be achieved. As with the first and second conductive gel members 80 and 82, the conductive gel member 88 may be electrically connected to a constant potential.

Figure 8:
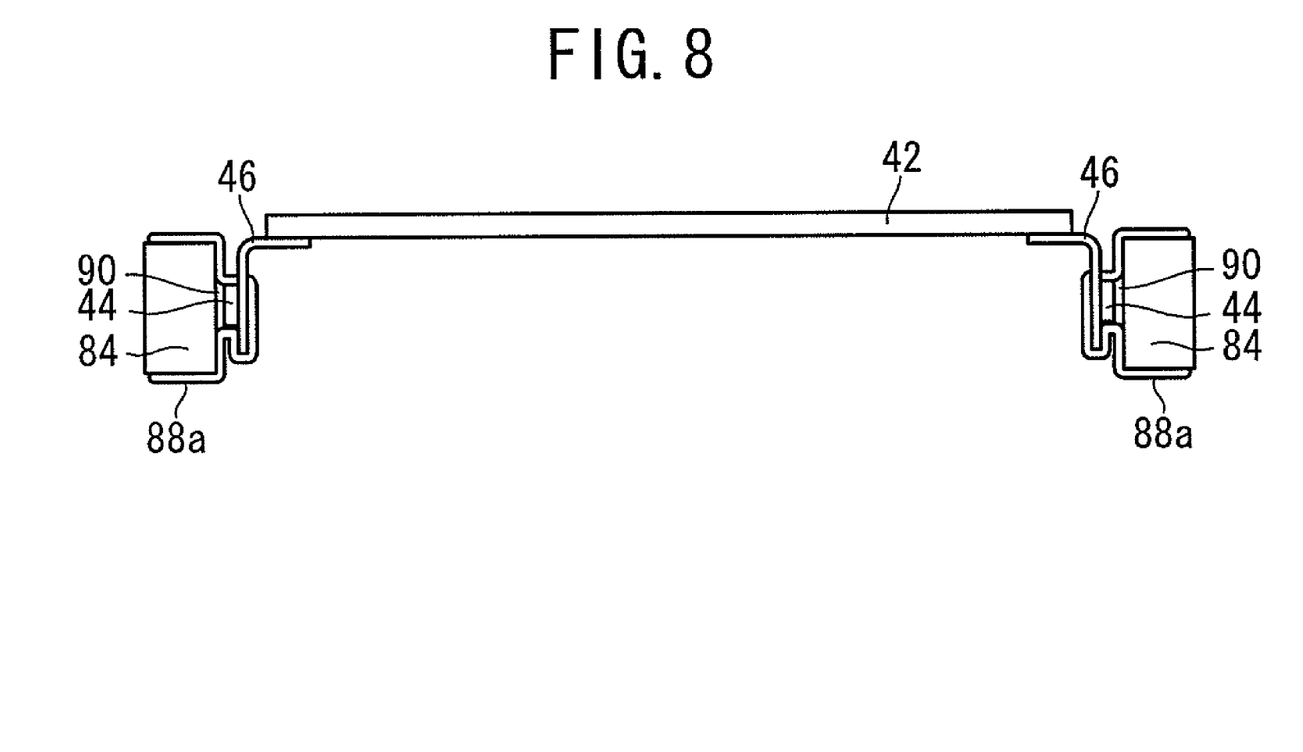
FIG. 8 is a schematic view of the radiation detector and the components therearound according to a second modification of the radiation image capturing apparatus of the invention.
Figure 9:
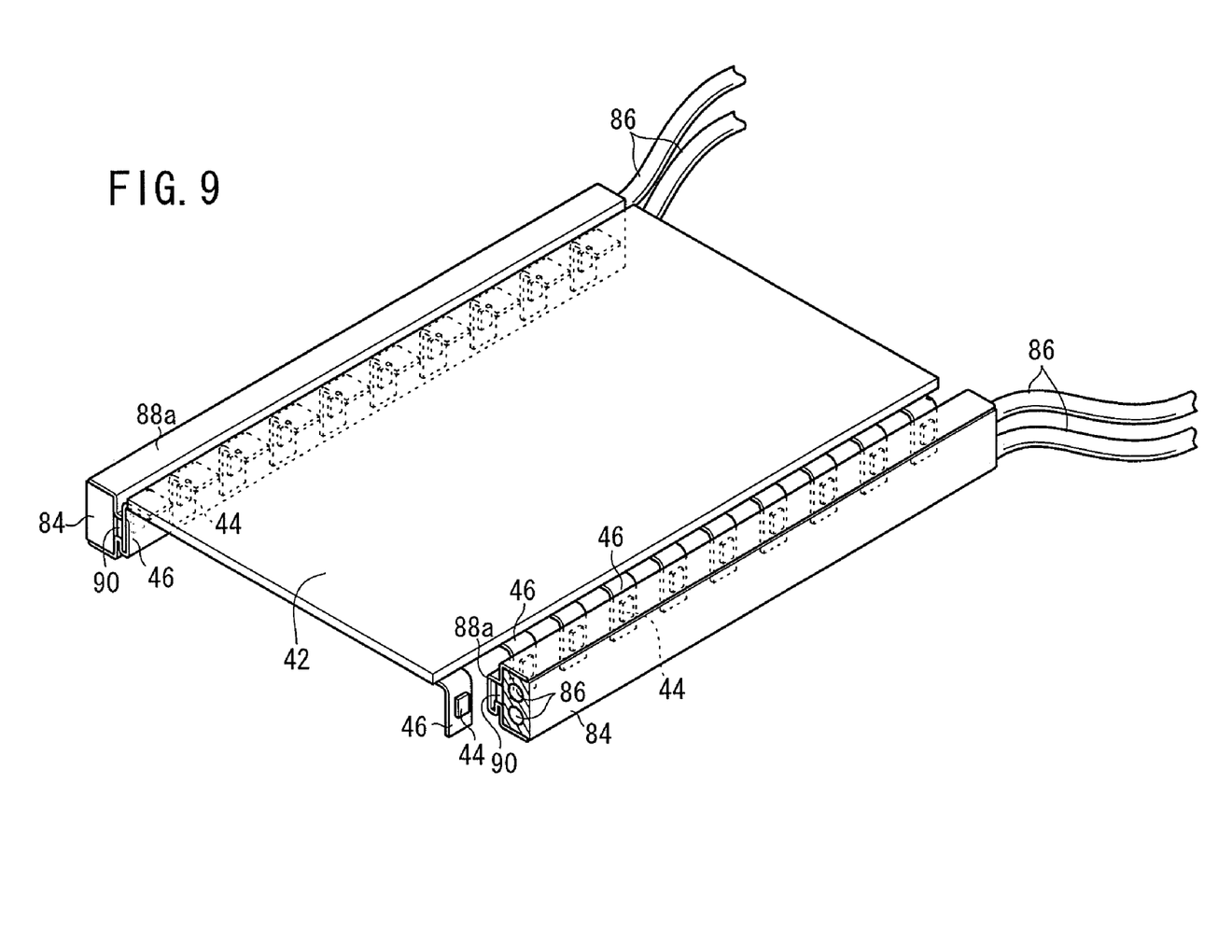
FIG. 9 is a partially cut-away perspective view of the radiation detector and the components therearound according to the second modification of the radiation image capturing apparatus of the invention.

FIGS. 8 and 9 illustrate another possible arrangement of the radiation detector 42, ASIC 44, and cooling jacket 84. In FIG. 7, the conductive gel member 88 extends below the ASIC 44 from the radiation detector 42 side to the cooling jacket 84 side. In FIG. 8, however, a conductive gel member 88a extends not only below but also over the ASIC 44 from the radiation detector 42 side to the cooling jacket 84 side. Thus, the conductive gel member 88*a* surrounds the ASIC 44 more completely and thus serves as a shield against electromagnetic noise more reliably. Further, it should be noted that, in FIG. 8, the conductive gel member 88*a* is in contact with the upper and lower surfaces of the cooling jacket 84, and a thermal conductive gel member 90, such as that disclosed in Japanese Laid-Open Patent Publication No. 2005-283262, is disposed between the ASIC 44 and the cooling jacket 84. Thus, in addition to blocking electromagnetic noise, the cooling efficiency of the ASIC 44 can be increased. As with the first and second conductive gel members 80 and 82, the conductive gel member 88*a* may be electrically connected to a constant potential.

Instead of to the housing 40, the first and second conductive gel members 80 and 82 may be electrically connected to other members of the mammography apparatus 20. For example, some of the electrodes on the flexible substrate 46, which electrically connects the ASIC 44 to the radiation detector 42, may be exposed so that the first and second conductive gel members 80 and 82 can be electrically connected thereto. Note that the electrodes of the flexible substrate 46 are designed to be at the same potential as that of the housing 40.

It should be also noted that the first and second conductive gel members 80 and 82 may be electrically connected to both of the housing 40 and the flexible substrate 46.

In the above-mentioned embodiment, the cooling jacket 84 is utilized to cool the ASIC 44. The cooling jacket 84, however, is not necessarily used.

What is claimed is:

1. A radiation image capturing apparatus, comprising:
   a radiation detector for detecting a radiation image of a subject as charge information and generating an electrical signal representing the charge information;
   an integrated circuit disposed in vicinity of the radiation detector and electrically connected thereto; and
   a conductive gel member disposed between the radiation detector and the integrated circuit.

2. The radiation image capturing apparatus according to claim 1, wherein the conductive gel member surrounds the integrated circuit.

3. The radiation image capturing apparatus according to claim 1, wherein the conductive gel member contains at least one of carbon and silver.

* * * * *